United States Patent
Bremnes et al.

(10) Patent No.: US 8,824,800 B2
(45) Date of Patent: Sep. 2, 2014

(54) IMMUNOASSAY ANALYSIS METHOD

(75) Inventors: Dag Bremnes, Høenefoss (NO); Eystein Ebeltoft, Oslo (NO)

(73) Assignee: Skannex AS, Hoenefoss (NO)

( * ) Notice: Subject to any disclaimer, the term of this patent is extended or adjusted under 35 U.S.C. 154(b) by 666 days.

(21) Appl. No.: 12/739,667

(22) PCT Filed: Oct. 23, 2008

(86) PCT No.: PCT/NO2008/000375
§ 371 (c)(1),
(2), (4) Date: Aug. 23, 2010

(87) PCT Pub. No.: WO2009/054729
PCT Pub. Date: Apr. 30, 2009

(65) Prior Publication Data
US 2011/0019883 A1 Jan. 27, 2011

(30) Foreign Application Priority Data
Oct. 23, 2007 (NO) .................................. 20075388

(51) Int. Cl.
*G06K 9/18* (2006.01)
*G06K 7/14* (2006.01)
*G06F 19/00* (2011.01)

(52) U.S. Cl.
CPC ................ *G06K 7/14* (2013.01); *G06K 7/1473* (2013.01); *G06F 19/366* (2013.01)
USPC ........... 382/183; 382/128; 382/176; 436/518; 436/287.2; 436/5; 436/34

(58) Field of Classification Search
CPC G06T 7/0012; G06F 19/321; G06K 9/00456; G06K 9/183; G01N 33/54366; G01N 33/558
USPC ............... 382/128, 176, 183; 436/518, 287.1, 436/287.2, 5, 34, 10.5
See application file for complete search history.

(56) References Cited

U.S. PATENT DOCUMENTS

| 4,632,901 A | 12/1986 | Valkirs et al. |
| 5,591,645 A | 1/1997 | Rosenstein |
| 5,602,040 A | 2/1997 | May et al. |

(Continued)

FOREIGN PATENT DOCUMENTS

| CN | 1773288 A | 5/2006 |
| DE | 10 2006 019 422 | 10/2007 |

(Continued)

OTHER PUBLICATIONS

Office Action for Application No. NO 20075388 dated Apr. 25, 2008.

(Continued)

*Primary Examiner* — Ruiping Li
(74) *Attorney, Agent, or Firm* — Alston & Bird LLP

(57) ABSTRACT

A method and system for analysis of immunoassays, and more specifically to an improved analysis of chromatographic assays, often referred to as a lateral flow assay is disclosed. These assays commonly employ a test strip utilizing visible particles as the labels for the analytes to be detected, where, as an additional feature, the analytical strip is removable for reading the quantity of analytes captured therein and for archival purposes. An image of the test strip is analyzed automatically.

22 Claims, 2 Drawing Sheets

(56) References Cited

U.S. PATENT DOCUMENTS

| | | | |
|---|---|---|---|
| 5,622,871 | A | 4/1997 | May et al. |
| 5,714,389 | A | 2/1998 | Charlton et al. |
| 5,798,273 | A | 8/1998 | Shuler et al. |
| 5,879,951 | A | 3/1999 | Sy |
| 5,958,790 | A | 9/1999 | Cerny |
| 6,129,278 | A | 10/2000 | Wang et al. |
| 6,136,549 | A | 10/2000 | Feistel |
| 6,770,487 | B2 | 8/2004 | Crosby |
| 2003/0116628 | A1 | 6/2003 | Nakazawa et al. |
| 2003/0170613 | A1* | 9/2003 | Straus ................ 435/5 |
| 2004/0232239 | A1 | 11/2004 | Tseng |
| 2005/0095697 | A1 | 5/2005 | Bachur, Jr. et al. |
| 2005/0249633 | A1 | 11/2005 | Blatt et al. |
| 2005/0288183 | A1 | 12/2005 | Sandra et al. |
| 2006/0008923 | A1 | 1/2006 | Anderson et al. |
| 2006/0014302 | A1* | 1/2006 | Martinez et al. .......... 436/518 |

FOREIGN PATENT DOCUMENTS

| | | |
|---|---|---|
| EP | 0 953 149 | 9/2004 |
| EP | 1 607 137 A2 | 12/2005 |
| EP | 1607134 A1 | 12/2005 |
| JP | H07-190940 A | 7/1995 |
| JP | 2003-121260 A | 4/2003 |
| JP | 2007-068083 A | 3/2007 |
| JP | 2007-101482 A | 4/2007 |

OTHER PUBLICATIONS

International Search Report for International Application No. PCT/NO2008/000375.

Written Opinion of the International Searching Authority for International Application No. PCT/NO2008/000375.

\* cited by examiner

IMMUNOASSAY ANALYSIS METHOD

FIELD OF THE INVENTION

The present invention relates generally to immunoassays, and more specifically to an improved analysis of chromatographic assays, often referred to as a lateral flow assay. IN PARTICULAR THE quantitative or semi-quantitative ANALYSIS OF LATERAL FLOW ASSAYS. These assays commonly employ a test strip utilizing visible particles as the labels for the analytes to be detected, where, as an additional feature, the analytical strip is removable for reading the quantity of analytes captured therein and for archival purposes.

BACKGROUND OF THE INVENTION/DESCRIPTION OF THE PRIOR ART

An immunoassay is a well known laboratory method used to determine the amount of an analyte in a sample such as plasma or urine. It is based on the interaction of antibodies with antigens, and because of the degree of selectivity for the analyte (either antigen or antibody), an immunoassay can be used to quantitatively determine very low concentrations of drugs, hormones, polypeptides, or other compounds found in a test sample. For many years, trained laboratory technicians performed immunoassays by hand.

Various chromatographic immunoassay techniques have been available for many years. One common aspect of known devices, particularly in the lateral flow technology, is that the assay is read visually, that is, by means of one or more optically readable lines on a test strip, typically held in a carrier, which may have various configurations. One end of the test strip is exposed to the sample, normally a body fluid of some type, being tested for the particular target analytes of interest. It is known that particular analytes are indicative of particular biological, environmental, and biohazard conditions, among others. For example, urine may be tested for pregnancy or ovulation and if the target analytes are present, the test is positive. Body fluids may be tested for the presence of other analytes indicative of biological conditions or they may be indicative of the presence of substances, such as drugs. Another example would be for testing water for contaminates. Examples of lateral flow assay methods and apparatus, where the reading is conducted optically, are shown in U.S. Pat. Nos. 5,591,645; 5,798,273; 5,622,871; 5,602,040; 5,714,389; 5,879,951; 4,632,901; and 5,958,790.

Recently, many companies have begun producing automated immunoassay analyzers. Automating the immunoassay procedures has been difficult because of the large number of steps that need to be performed. For example, a sample is mixed with a reagent and a solid support having a bound antigen or antibody, the sample is incubated such that the corresponding antigen or antibody in the sample and a labelled antigen or antibody provided in the reagent can be bound to the antigen or antibody on the solid support, then the solid support is thoroughly washed and the label (fluorescent, radioactive, chemiluminescent, or the like) is detected by an appropriate mechanism, and finally the analyte of interest (antigen or antibody) is quantified from the detected label.

One of the problems with reading of Lateral flow cassettes and also other similar cassettes is the lack of a true general reader. All of the readers on the market today are designed for a group of cassettes with similar properties. A consequence is that the user needs to use different instruments with different shape, user interface and connection to printer and journal systems. The lack of a general instrument limits the possibility to use low cost measurement cassettes.

A general instrument must be able to process cassettes of different shapes and colours. A scanner or camera-based system can be able to read cassettes of different shape as long as it is possible to locate the cassette on a scanner plate or another suitable place for a capturing a camera image. The contrast between the cassette and the background can be high or low dependent of the colour of the cassette and the colour of the background. The image can also contain shadows at the edge of the cassette. The image can be out of focus, or be distorted. A scanner plate background is normally either black or white, but when scanning with the scanner lid lifted up (the cassette is not completely flat), the image can also contain ambient lightning from light sources outside the scanner. The background when capturing a camera image can be anything the user finds suitable. Ambient lightning can also be difficult to control when capturing a camera image of a device.

Use of barcodes is becoming more widespread; including use of barcodes for identifying many different types of things, including, but not limited to commercial goods, such as groceries, product packages of various types, printed reading material. A barcode typically assigns a unique identifier to a particular commodity.

A barcode is a graphic identifier used to encode a set of digits or characters. A barcode comprises a series of bars and spaces, which may have different widths according to various encoding rules, such as the standard commodity barcode EAN13 barcode specification.

In the bio-medical field a barcode has been described as to convey specific information about a patient, including clinical history and as a unique identifier of the patient sample, in addition to the categorization of the assay being conducted on the patient sample as well as for tracing and control purposes.

From the abovementioned, it will be appreciated that there remains a need in the art for a general, simple, effective means to locate, calibrate and identify biological test devices.

DETAILED DESCRIPTION OF THE INVENTION

Figure 1:
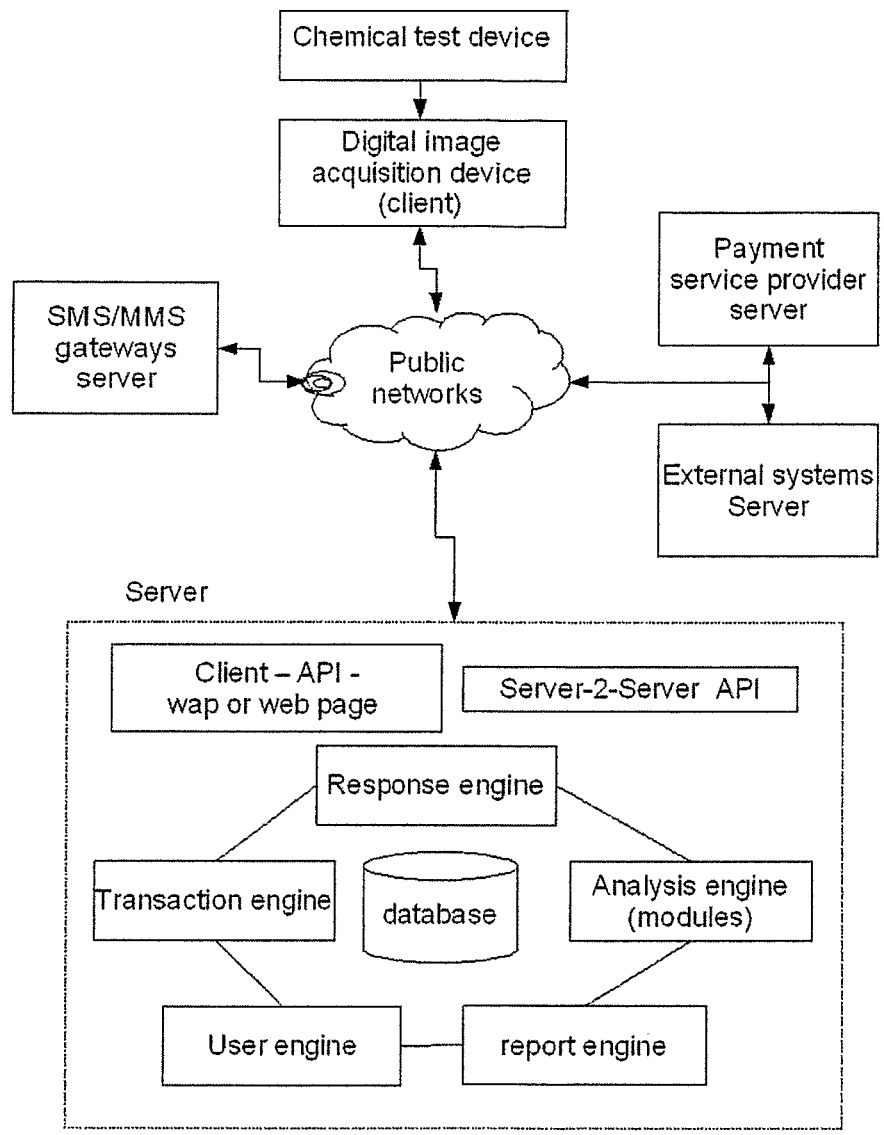
FIG. 1 illustrates an example of embodiment of a system according to the present invention.

According to an aspect of the present invention, reading a lateral flow test strip as described above may be done with a scanner device. However, distortion of the scanned image, which often is the case with seamier technology, may introduce errors when measuring the test strip. It is well known in prior art how to identify an object in a scanned image. The lines that are the result of the test are easily identified with such prior art techniques. However, the accuracy of the test is dependent on the geometrical location of the lines. It is the relative position on the lateral test strip surface of these lines that provides the test result. Therefore, any introduced geometrical distortion of the scanned image may provide false or inaccurate test results. However, if the image comprises an object that can reveal the amount of distortion present in the scanned image, geometrical image analysis methods as known to a person skilled in the art may be applied to restore the scanned image to a correctly sized picture of the test strip surface. When this corrected image is used to identify the lines that are the result of the test, accurate test results may be obtained automatically.

According to an example of embodiment of the present invention, bar codes may be used to reveal geometrical distortions, and also provide means for identifying the amount of distortion and then provide a possibility to correct the image.

For example, a bar code segment comprising information about the test strip is printed on the surface of the test strip, and the bar code and its information can be stored in a database together with relevant information such geometrical size of the barcode coded text segment etc. According to this example of embodiment, a proprietary bar code system provides a special design of the barcodes for correcting systematically measurement errors of the white and black bars (or other colours with acceptable contrast) on the barcode. The barcode will always contain equal area of black and white bars. Typically, the measurement can create barcode bars in the image that are thinner or wider than the real bars. Normally the translation from black to white or from white to black can be modelled as an s curve. The translation from black to white is not necessary symmetrical with the translation from white to black. A consequence is wrong size of white and black bars. Since the true amount of black and white is equal, the system then can measure the amount of black and white and then do a correction. This information can also be used to make a correction of the control and measurement lines on the cassette.

The barcode contains at least one line of information. It can contain as many lines as necessary. Each barcode line contains a fixed number of barcode modules defining the black and white bars. Each bar contains one or more barcode modules. When the system has detected the start and stop position of the barcode, the module width can be computed. From the module width, the length of black and white bars and a barcode alphabet it is possible to compute the barcode symbols for all the barcode lines. The first information on the barcode is the identification of the cassette. A corresponding database contains information for this cassette including the physical length of the barcode. Since the system has found the length of the barcode (in pixels) and the database contains the physical distance, it is possible to compute DPI (dots per inch) of the image. This is important because the lighting, imaging, and focusing conditions of a camera cannot readily be controlled.

From the lower left corner of the barcode, the orientation of the barcode, the estimated DPI and information in the cassette database describing the distance from the barcode left corner to measurement area, it is possible to define a local search area containing all interesting measurement objects. In the local search area the system can search for lines or other measurement objects. The only necessary part of a cassette is the barcode area and the measurement areas. A consequence is that other parts of the cassette do not have to be inside the image. When capturing an image with a camera, only a small part of the cassette must be captured. Then even with a low-resolution camera it is possible to get enough pixels to be able to read both the barcode and also the measurement area.

According to another aspect of the present invention, calibration of an image system is necessary to perform as a relative measurement since there is no control of light sources. A single signal alone (e.g. strength of a line) is not enough. Since lateral flow cassettes usually have a control line connected to each test line it is possible to compute a relative measurement=(strength of test line)/(strength of control line). Since the control and test line are both measured using the same light source and sensor, the relative measurement is also a calibration, therefore there is no requirement for specific calibration objects.

When cassettes of the same type and production batch are processed using the same scanner, we can eliminate some of the control line noise by computing a mean control line based on many control line measurements.

The barcode can also contain more than geometrical/optical information. Typical the barcode will contain cassette identification, lot number, expiry date and for each measurement area: standard curves or qualitative thresholds. All necessary information is contained on the barcode. The user only needs to run the chemical/biological processing according to the cassette package insert. After sample is applied on a cassette, the program can take care of incubation time and perform the necessary delay before scanning. Normally the system will perform a scan after the shortest possible incubation time defined in the cassette database. After the first scan the system will know the identification of all cassettes in the image. The system can then make a decision of eventually the next scan time.

The present invention may be embodied using a decentralized or centralized context based on a /client-server/ type of network architecture in which data can be exchanged through a request and response syntax.

The scanner or the camera will be used only as image capture devices, also called a /client/. The client will not compute the result, however only be used as a capturing device.

In a centralized client-server setup, the client may also be the only user interface, and display data (result from the analysis) from the server. That is, if a display on the client is available.

In decentralized or localized setup, both client and server may be physically attached. In such setup, the server may be the unit that controls and drives the display and handle the user interface.

In a first embodiment the client may be a scanner connected to a computer, in which the latter is the /server/ doing all the processing and handles the user interface. The connection between the scanner and the server may use any known and available physical network and protocol, such as USB, Wifi (etc)

In another example of embodiment the /client/ may be a camera, preferably a cell phone camera, which can communicate with the server using e.g. MMS and SMS messages in a GSM type of network. Alternatively the server can for registered users, send a result back using other information channels like e-mail. A payment transaction can also be to included in the MMS/SMS message transaction.

The client, dependent on where the user interface is, will:
receive a request from the server to capture and upload an image, or the contrary, upload an image to the server.
receive data from the server
The server will:
make a request to or handle a request from client to receive an image
analyze image and make available the result at a local display, alternatively push a response back to the client. The latter requires the client to have a suitable display unit (e.g. mobile phone)

SUMMARY

The /client/ is defined as the apparatus which is used to capture and send the image. This may be any device and this invention allows acting as a 'dumb' device which does not carry out any local processing for the purpose of analyzing the image. The client apparatus is not instructed by the server to perform any local settings. Unlike other remote controlled systems this invention will allow centralized analysis to be performed on any image.

The /server is a complete set of software modules which is installed on a computer that is connected to any type of digital network. Such a server can thereby handle requests from any type of /clients/. The server can e.g. allow for controlled log on of a user, or it can allow for anonymous use. In either case the server automatically logs or registers the address (number) of the client (telephone), and will then start analyzing the image received. The application may control transactions tied to the request and response regime, and the analysis. An advantage is that software upgrades will be very easy to perform.

Example:

Lateral Flow cassette measuring Calprotectin from Calpro AS using a scanner. Image is being processed in a connected PC 1. Apply samples on a set of cassettes
2. Click program button immediately after sample is applied on last cassette
3. Program will scan after 5 minutes
4. Find a barcode candidate, if no more found, go to 24
5. Find frame around barcode
6. Find barcode module size
7. Find length of each black/white bar
8. Accumulate length of all black bars, SumB
9. Accumulate length of all white bars, SumW
10. Compute mean bar length, MeanB and MeanW for black and white bars
11. Define correction Corr=(MeanB−MeanW)/2
12. Add Corr to length of all white bars
13. Subtract Corr from length of all black bars
14. Find barcode string
15. Find cassette ID
16. Get barcode length from cassette database and compute DPI
17. Find control line search area
18. Find control line inside search area
19. Find test line search area relative to control line
20. Find control line inside search area
21. Compute strength of control line relative to local background
22. Compute strength of test line relative to local background
23. Go to 4.
24. Compute mean control line (meanControl) from all found cassettes from same lot.
25. Read old mean control line (oldControl) from file.
26. ControlLine=(n*meanControl+m*oldControl)/(n+m)
27. Where n=number cassettes, m=predefined weight (for example 20)
28. Save ControlLine to file
29. For each cassette:
a. Compute p=testline/ControlLine
b. Use standard curve from barcode to interpolate final Calprotectin value Example:

LateralFlow cassette measuring Calprotectin from Calpro AS using a cellphone. Image is transferred via MMS to a central server.

Same as for camera, but for each cassette the used control line is the measured control line, not mean from many control lines Example:

LateralFlow cassette measuring DON from R-Biopharm using a scanner

Normally the control line is independent of amount of analyte. The DON cassette is different. Control line is also dependent of amount of analyte. The processing of DON cassettes on a scanner is equal to processing of Calprotectin from cellphone. No control mean is used.

Figure 2:
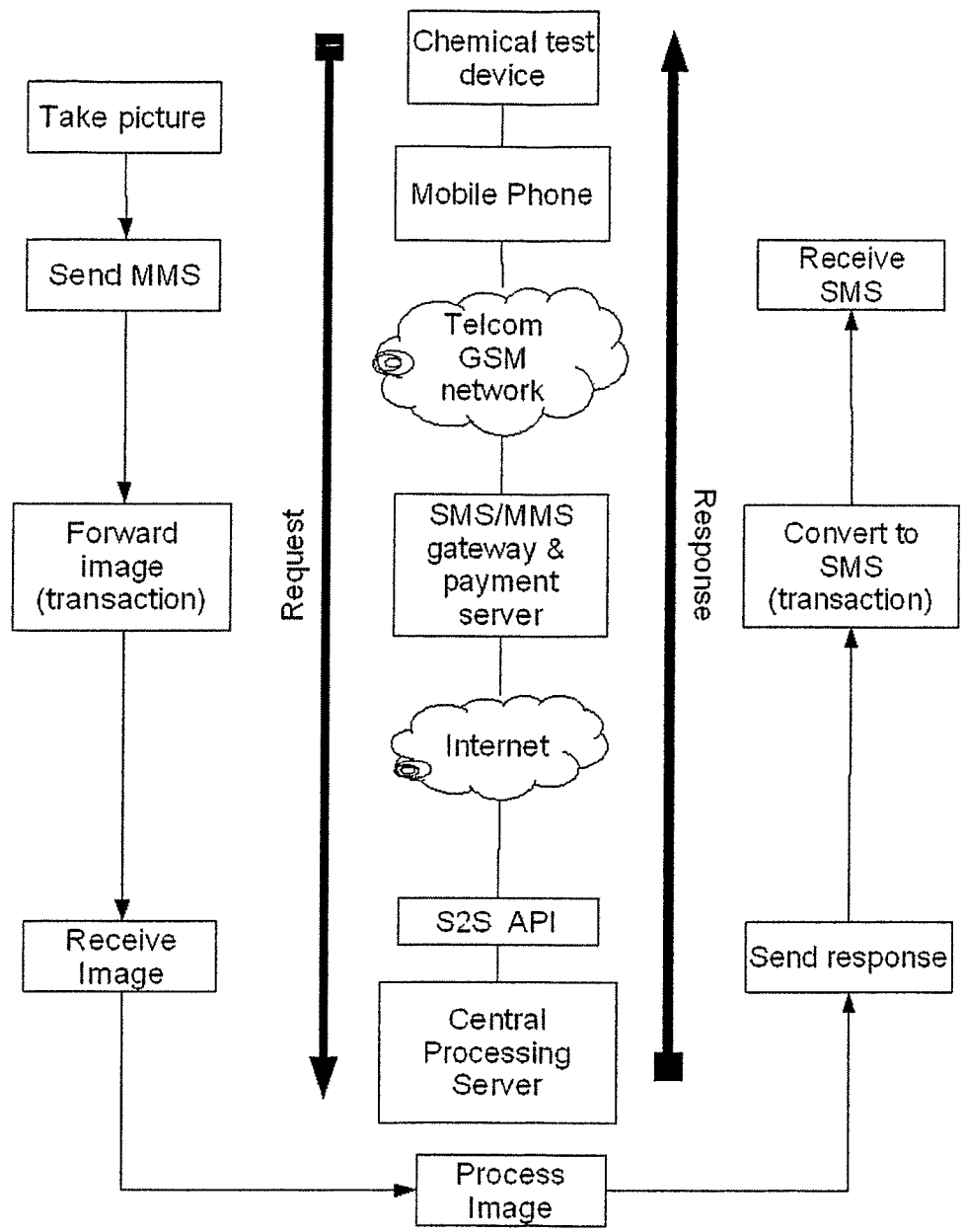
FIG. 2 illustrates another example of embodiment of a system according to the present invention.

FIG. 1 illustrates an example of an embodiment of the present invention. A chemical test device (lateral flow test strip) to a digital image acquisition device (client) that for example can communicate over a public network, for example the Internet or a mobile telephone network. For example, a MMS picture may be sent to the server providing access to a database comprising information about bar code coded text segments according to the present invention. A response to the analysis result can be provided back to a user of the system, for example as a SMS message. FIG. 2 illustrates another example of embodiment of the present invention wherein a mobile telephone is used to acquire a picture of an immunoassay test. The picture is sent as an MMS message before being processed, for example in a central processing server. The response is sent as a SMS message back to the user.

The invention claimed is:

1. A method for semi-quantitative or quantitative analysis of a plurality of assays, wherein the method comprises:
   assigning at least one unique barcode coded text segment on a first portion of at least one of a test strip or a cassette of at least one of the plurality of assays, the at least one of the test strip or the cassette further comprising a second portion distinct from the first portion, the second portion comprising at least a response zone and a control zone;
   acquiring an image of at least one of the test strip and the cassette, the image comprising the at least one unique barcode coded text segment and at least one test result line in the response zone, the at least one test result line being generated by the at least one of the plurality of assays;
   identifying the at least one unique barcode coded text segment in the acquired image and using the identified barcode coded text segment as an optical calibration entity;
   using the optical calibration entity and geometric information from a database to detect a search area of at least one control line in the control zone; and
   using an identified position of the at least one control line and the geometric information from the database to detect a search area for the at least one test result line.

2. The method according to claim 1, wherein using the optical calibration entity comprises using a barcode coding scheme for the coding of text providing equal area of white space and black space in a bar coded text segment.

3. The method according to claim 1, wherein using the optical calibration entity comprises
   identifying the unique text comprised in the at least one barcode coded text segment, and using the unique text to identify a pre-stored version of the identified text together with information about a geometrical position and orientation of the barcode coded text segment that has been identified.

4. The method according to claim 1, wherein the assay is an immunoassay.

5. The method according to claim 4, wherein the immunoassay is a lateral flow chromatographic test strip.

6. The method according to claim 1, wherein the geometric information from the database comprises a control line intensity based at least in part upon a mean of control line intensities generated from a plurality of measured control lines.

7. The method according to claim 1, wherein acquiring an image comprises acquiring an image using an imaging system, and wherein the imaging system comprises a scanner connected to a computer or network.

8. The method according to claim 1, wherein acquiring an image comprises acquiring an image using an imaging system, and wherein the imaging system comprises a camera connected to a computer or network.

9. The method according to claim 1, wherein acquiring an image comprises acquiring an image using an imaging system, and wherein the imaging system comprises a mobile phone camera connected to a computer or network.

10. The method according to claim 7, wherein the imaging system can communicate with a server via any available network.

11. The method according to claim 1, wherein the at least one barcode coded text segment comprises assay or sample recognition parameters.

12. A system for semi-quantitative or quantitative analysis of a plurality of assays, wherein the system comprises:
   at least one computer device being arranged to execute program instructions providing actions and functions according to a method for semi-quantitative or quantitative analysis of each of the plurality of assays, wherein the method comprises:
      assigning at least one unique barcode coded text segment on a first portion of at least one of a test strip or a cassette of at least one of the plurality of assays, the at least one of the test strip or the cassette further comprising a second portion distinct from the first portion, the second portion comprising at least a response zone and a control zone;
      acquiring an image of the at least one of the test strip and the cassette, the image comprising the at least one unique barcode coded text segment and at least one test result line in the response zone, the at least one test result line being generated by the at least one of the plurality of assays;
      identifying the at least one unique barcode coded text segment in the acquired image and using the identified barcode coded text segment as an optical calibration entity;
      using the optical calibration entity and geometric information from a database to detect a search area of at least one control line in the control zone; and
      using an identified position of the at least one control line and the geometric information from the database to detect a search area for the at least one test result line.

13. The system according to claim 12, wherein using the optical calibration entity comprises using a barcode coding scheme for the coding of text providing equal area of white space and black space in a bar coded text segment.

14. The system according to claim 12, wherein using the optical calibration entity comprises
   identifying the unique text comprised in the at least one barcode coded text segment, and using the unique text to identify a pre-stored version of the identified text together with information about a geometrical position and orientation of the barcode coded text segment that has been identified.

15. The system according to claim 12, wherein the assay is an immunoassay.

16. The system according to claim 15, wherein the immunoassay is a lateral flow chromatographic test strip.

17. The system according to claim 12, wherein the geometric information from the database comprises a control line intensity based at least in part upon a mean of control line intensities generated from a plurality of measured control lines.

18. The system according to claim 12, wherein acquiring an image comprises acquiring an image using an imaging system, and wherein the imaging system comprises a scanner connected to a computer or network.

19. The system according to claim 18, wherein the imaging system can communicate with a server via any available network.

20. The system according to claim 12, wherein acquiring an image comprises acquiring an image using an imaging system, and wherein the imaging system comprises a camera connected to a computer or network.

21. The system according to claim 12, wherein acquiring an image comprises acquiring an image using an imaging system, and wherein the imaging system comprises a mobile phone camera connected to a computer or network.

22. The system according to claim 12, wherein the at least one barcode coded text segment comprises assay or sample recognition parameters.

* * * * *